United States Patent
Fürstner et al.

(10) Patent No.: US 6,590,048 B1
(45) Date of Patent: Jul. 8, 2003

(54) HIGHLY ACTIVE CATIONIC RUTHENIUM AND OSMIUM COMPLEXES FOR OLEFIN METATHESIS REACTIONS

(75) Inventors: Alois Fürstner, Ruhr (DE); Pierre Dixneuf, Rennes (DE); Christian Bruneau, Thorigné-Fouillard (FR); Michel Picquet, Dijon (FR)

(73) Assignee: Studiengesellschaft Kohle mbH (DE)

( * ) Notice: Subject to any disclaimer, the term of this patent is extended or adjusted under 35 U.S.C. 154(b) by 0 days.

(21) Appl. No.: 09/555,652
(22) PCT Filed: Nov. 17, 1998
(86) PCT No.: PCT/EP98/07364
§ 371 (c)(1), (2), (4) Date: Jan. 2, 2001
(87) PCT Pub. No.: WO99/28330
PCT Pub. Date: Jun. 10, 1999

(30) Foreign Application Priority Data

Dec. 3, 1997 (EP) .............................................. 97121228

(51) Int. Cl.[7] .............................. C07C 6/04; C07F 15/00
(52) U.S. Cl. ....................... 526/171; 526/281; 526/283; 526/308; 525/245; 549/267; 549/347; 556/13; 556/22; 556/32; 556/136; 568/338; 568/361; 585/365; 585/643
(58) Field of Search ................................ 526/171, 281, 526/308, 283; 525/245; 556/13, 22, 32, 136; 585/365, 643; 549/267, 347; 568/338, 361

(56) References Cited

U.S. PATENT DOCUMENTS 5,936,100 A * 8/1999 Furstner et al. ............. 549/266

FOREIGN PATENT DOCUMENTS

| DE | 44 47 066 A | 7/1996 |
|----|-------------|--------|
| WO | WO 93/20111 | 10/1993 |
| WO | WP 96/04289 | 2/1996 |
| WO | WO 97/06185 | 2/1997 |

* cited by examiner

Primary Examiner—Fred Teskin
(74) Attorney, Agent, or Firm—Norris McLaughlin & Marcus

(57) ABSTRACT

The present invention describes the use of cationic vinylidene, allenylidene and higher cumulenylidene complexes of ruthenium or osmium as catalysts or catalyst precursors for olefin metathesis reactions of all types, as well as to new cationic allenylidene complexes of ruthenium and osmium which can be used as metathesis catalysts with preferred embodiment. These catalysts or catalyst precursors are easy to prepare from well accessible, stable and essentially non toxic starting materials, can be isolated and stored, they exhibit a high catalytic activity, a good compatibility with functional groups, solvents, water and additives, and they need not to be activated by any additive. Olefins of all types can be used as the substrates in the present invention in ring closing metathesis (RCM) of acyclic dienes and polyenes, the metathesis of enynes and dienynes, the ring opening metathesis polymerization (ROMP) of cyclic olefins, the acyclic diene metathesis polymerization (ADMET) of acyclic dienes or polyenes, the depolymerization of olefinic polymers, and the cross metathesis of two or more olefins. The present invention also applies to combinations of these types of metathetic reactions and domino processes thereof.

29 Claims, No Drawings

HIGHLY ACTIVE CATIONIC RUTHENIUM AND OSMIUM COMPLEXES FOR OLEFIN METATHESIS REACTIONS

This application is a 371 of PCT/EP98/07364, filed on Nov. 17, 1998.

BACKGROUND OF THE INVENTION

The present invention describes the use of cationic vinylidene, allenylidene and higher cumulenylidene complexes of ruthenium or osmium as catalysts or catalyst precursors for olefin metathesis reactions of all types. The present invention also relates to new cationic allenylidene complexes of ruthenium and osmium which can be used as metathesis catalysts with preferred embodiment. These catalysts or catalyst precursors are easy to prepare from well accessible, stable and essentially non toxic starting materials, can be isolated and stored, they exhibit a high catalytic activity, a good compatibility with functional groups, solvents, water and additives, and they need not to be activated by any additive. Olefins of all types can be used as the substrates in the present invention.

PRIOR ART

Olefin metathesis refers to the interchange of carbon atoms between a pair of double bonds. Reactions of this type have found applications to processes of industrial importance (Reviews: Ivin, K. J.; Mol, J. C. *Olefin Metathesis and Metathesis Polymerization*, Academic Press, New York, 1997; Schuster, M. et al., *Angew. Chem.* 1997, 109, 2125). Olefin metathesis reactions are catalyzed by various metal compounds. Many of the classical catalysts consist of mixtures of various components, they are ill defined in their chemical composition, show a poor compatibility with functional groups and are inefficient as a consequence of little active species present. More modern catalysts or catalyst precursors with a better application profile comprise complexes of the general types I–IX: (references: type I (M=Ru, Os): WO 96/04289, 15.02.1996; Nguyen S. T. et al. *J. Am. Chem. Soc.* 1992, 114, 3974; Nguyen S. T. et al. *J. Am. Chem. Soc.* 1993, 115, 9858; Schwab, P. et al. *Angew. Chem.* 1995, 107, 2179 (*Angew. Chem. Int. Ed. Engl.*, 1995, 34, 2039); Schwab, P. et al. *J. Am. Chem. Soc.* 1996, 118, 100; Mohr, B. et al. *Organometallics* 1996, 15, 4317; Wilhelm, T. E. et al. *Organometallics* 1997, 16, 3867; Belderrain, T. R. *Organometallics* 1997, 16, 4001. Type II (M=Mo, W): Schrock, R. R. et al. *J. Am. Chem. Soc.* 1990, 112, 3875; Fujimura, O. et al. *Organometallics* 1996, 15, 1865. Type III: Quignard, F. et al. *J. Mol. Catal.* 1986, 36, 13. Type IV (M=Nb, Ta): Rocklage, S. M. et al. *J. Am. Chem. Soc.* 1981, 103, 1440; Wallace, K. C. et al. *Macromolecules* 1987, 20, 448. Type V (cp=cyclopentadienyl or substituted cyclopentadienyl): U.S. Pat. No. 4,567,244, 28.01.1986. Type VI: Herrmann, W. A. et al. *Angew. Chem.* 1991, 103, 1704. Type VII: Nugent, W. A. et al. *J. Am. Chem. Soc.* 1995, 117, 8992. Type VII: Davie E. S. *J. Catal.* 1972, 24, 272. Type IX: Herrmann, W. A. et al. *Angew. Chem.* 1996, 108,1169.)

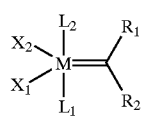

I

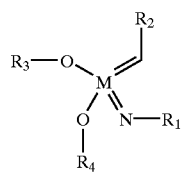

II

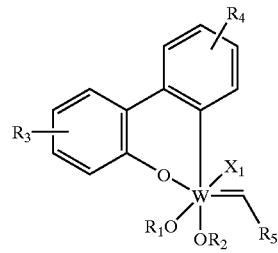

III

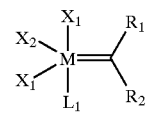

IV

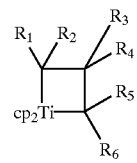

V $R_1$—$ReO_3$

VI $WO(X_1)_2(OR_1)_2/PbEt_4$

VII $Mo(CO)_6/Al_2O_3$

VIII

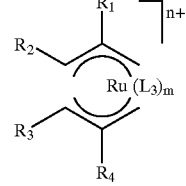

IX

A major disadvantage of these complexes relates to their preparation which requires either reagents which are hazardous (e. g. type I: diazoalkanes), or difficult to prepare (e.g. type I: diphenylcyclopropene), or extremely sensitive (e. g. type II, III, IV, V, VI). Another disadvantage relates to the fact that some of these metathesis catalysts themselves are very sensitive to oxygen, moisture and/or polar functional groups and must be handled with great care under a strictly inert athmosphere (e. g. types II, III, IV, V). Another disadvantage relates to the fact that some of these complexes exhibit a reasonable reactivity only after activation with an additive, which can either be hazardous (e. g. for type IX: diazoalkanes) or toxic (e. g. for type VII: PbEt$_4$). Catalysts of type VI are active only when deposited on special oxidic supports. Therefore a stringent need for metathesis catalysts persists, which reach or surpass the activity of the best catalysts I–IX described to date, but which are more readily accessible, require no hazardous reagents for their preparation, are robust, easy to isolate and handle, and need not be activated by any hazardous or toxic additives.

DETAILED DESCRIPTION OF THE INVENTION

The present invention, meets the criteria mentioned above. Surprisingly we find that cationic vinylidene, allenylidene and higher cumulenylidene complexes of ruthenium or osmium are highly efficient catalysts or catalyst precursors for olefin metathesis reactions of all types. These catalysts or catalyst precursors are easy to prepare from well accessible, stable and essentially non toxic starting materials, can be isolated and stored, they exhibit a high catalytic activity, a good compatibility with functional groups, solvents, water and additives, and they need not to be activated by any additive. Of the catalysts mentioned above, compounds of the general type XII, as specified below, are new compounds.

Specifically, the present invention relates to the use of vinylidene, allenylidene and higher cumulenylidene complexes of the general formula X as catalysts in olefin metathesis reactions of all types

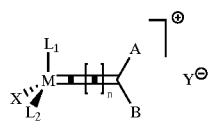

X wherein
- M is Ru or Os;
- X can be selected from any anionic ligand;
- $L_2$ can be selected from any type of phosphine, sulfonated phosphine, fluorinated phosphine, functionalized phosphine bearing up to three aminoalkyl-, ammoniumalkyl-, alkoxyalkyl-, alkoxycarbonylalkyl-, hydroxycarbonylalkyl-, hydroxyalkyl-, ketoalkyl-groups, phosphite, phosphinite, phosphonite, arsine, stibene.
- $L_1$ can be selected from any neutral π-bond ligand, preferably arene, substituted arene, heteroarene, independent of whether they are mono- or polycyclic;
- A, B can be independently selected from hydrogen or a hydrocarbon from the group consisting of C1–C20 alkyl, aryl, C2–C20 alkenyl, alkynyl, C1–C20 alkoxy, carboxylate, carbamate, C2–C20 alkenyloxy, alkynyloxy, aryloxy, alkoxycarbonyl, C1–C20 alkylthio, alkylsulfonyl, alkylsulfinyl, arylthio, arylsulfonyl, arylsulfinyl, alkylamido, alkylamino, each of which may be substituted with C1–C10 alkyl, perfluoroalkyl, aryl, alkoxy or with halogen;
- $Y^-$ may be selected from any non-coordinating anion;
- n is 0–5;

in a preferred embodiment:
- M is Ru or Os
- X is halogen
- $L_2$ is selected among phosphines bearing one or more secondary alkyl, tertiary alkyl, or cycloalkyl groups, preferably P(isopropyl)$_3$, P(cyclohexyl)$_3$, P(cyclopentyl)$_3$, P(neopentyl)$_3$, P(tertiobutyl)$_3$.
- $L_1$ is benzene or a substituted benzene derivative bearing up to six substituents which may be identical or not identical and can be independently selected from C1–C20 alkyl, aryl, alkoxy, aryloxy, alkylsulfonyl, arylsulfonyl, perfluoroalkyl, alkylthio, alkenylthio, C2–C10 alkenyl, alkynyl, alkenyloxy, alkynyloxy, or halogen, most preferably $L_1$ is toluene, xylene, cymene, trimethylbenzene, tetramethylbenzene, hexamethylbenzene, tetraline, naphthalene, or polycyclic arenes and their derivatives.
- $Y^-$ is selected from PF$_6^-$, BF$_4^-$, BPh$_4^-$, F$_3$CSO$_3^-$, H$_3$CSO$_3^-$, ClO$_4^-$, SO$_4^-$, NO$_3^-$, PO$_4^-$, CF$_3$COO$^-$, B(C$_6$F$_5$)$_4^-$, RSO$_3^-$, RCOO$^-$ with R being selected from C1–C20 alkyl, aryl
- n is 1.

The most preferred catalysts of the present invention include XI

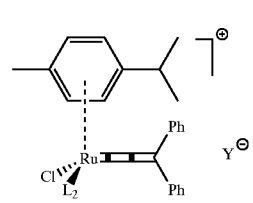

XI wherein
- $L_2$ can be selected from P(isopropyl)$_3$, P(cyclohexyl)$_3$, P(cyclopentyl)$_3$, P(neopentyl)$_3$, P(tertiobutyl)$_3$
- $Y^-$ is selected from PF$_6^-$, BF$_4^-$, BPh$_4^-$, F$_3$CSO$_3^-$, H$_3$CSO$_3^-$, ClO$_4^-$, SO$_4^-$, NO$_3^-$, PO$_4^-$, CF$_3$COO$^-$, B(C$_6$F$_5$)$_4^-$, RSO$_3^-$, RCOO$^-$ with R being selected from C1–C20 alkyl, aryl The preparation of these catalysts can be achieved by following the approach described in: Pilette, D. et al., *Organometallics* 1992, 11, 809.

The present invention also relates to new compounds of the general type XII

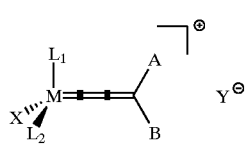

XII wherein
- M is Ru or Os
- X can be selected from any anionic ligand;
- $L_1$ can be selected from any neutral π-bond ligand, preferably arene, substituted arene, heteroarene, independent of whether they are mono- or polycyclic;
- $L_2$ is selected among phosphines, arsine or stibenes bearing one or more secondary alkyl, tertiary alkyl, or cycloalkyl groups;
- A, B can be independently selected from hydrogen or a hydrocarbon from the group consisting of C1–C20 alkyl, aryl, C2–C20 alkenyl, alkynyl, C1–C20 alkoxy, carboxylate, carbamate, C2–C20 alkenyloxy, alkynyloxy, aryloxy, alkoxycarbonyl, C1–C20 alkylthio, alkylsulfonyl, alkylsulfinyl, arylthio, arylsulfonyl, arylsulfinyl, alkylamido, alkylamino, each of-which may be substituted with C1–C10 alkyl, perfluoroalkyl, aryl, alkoxy or with halogen;
- $Y^-$ may be selected from any non-coordinating anion.

Compounds of the general type XII can be used as catalysts for olefin metathesis reactions according to the present invention. In a preferred embodiment
- M is Ru
- X is halogen
- $L_1$ is benzene or substituted benzene $L_2$ is selected among phosphines, arsine or stibenes bearing one or more secondary alkyl, tertiary alkyl, or cycloalkyl groups A, B can be independently selected from a hydrocarbon from the group consisting of C1–C20 alkyl, aryl, $Y^-$ may be selected from any non-coordinating anion.

Compounds of the general type XII can be used as most preferred catalysts for olefin metathesis reactions according to the present invention, wherein M is Ru X is chloride $L_1$ is p-cymene $L_2$ is selected among P(isopropyl)$_3$, P(cyclohexyl)$_3$, P(cyclopentyl)$_3$, P(neopentyl)$_3$, P(tertiobutyl)$_3$.

A, B are aryl or substituted aryl $Y^-$ may be selected from $PF_6^-$, $BF_4^-$, $BPh_4^-$, $F_3CSO_3^-$, $H_3CSO_3^-$, $ClO_4^-$, $SO_4^-$, $NO_3^-$, $PO_4^-$, $CF_3COO^-$, $B(C_6F_5)_4^-$, $RSO_3^-$, $RCOO^-$ with R being selected from C1–C20 alkyl, aryl.

The synthesis of compounds of the general type XII can be achieved according to Equation 1; examples for the preparation of compounds of the general type XII which serve as catalysts with most preferred embodiments according to the present invention are described in Examples 1 and 2. The ease of this preparation is a distinct advantage for the process of this invention over the processes of the prior art. Another major advantage relates to the fact that all hazardous, unstable and difficult to handle reagents are avoided which were previously used for the preparation of highly performing metathesis catalysts. This refers particularly to diazoalkanes and cyclopropene derivatives which are avoided in the catalysts used in the present invention. The fact that the cationic ruthenium or osmium complexes of the general type X–XII must not be activated by addition of diazoalkanes distinguishes them from other metathesis catalysts presently used, in particular from the cationic bisallylruthenium (+4) complexes of the general type IX previously described in the literature (Herrmann, W. A. et al. Angew. Chem. 1996, 108, 1169).

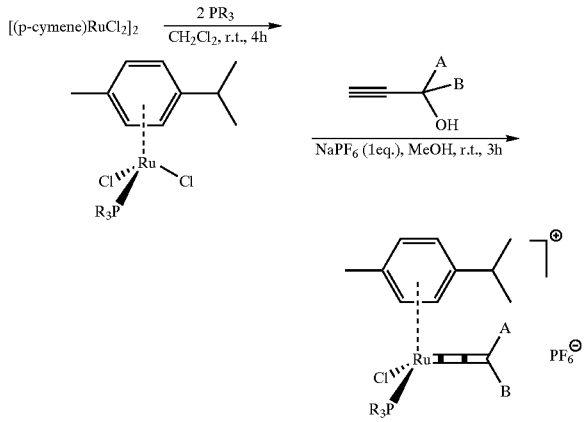

Equation 1. Example for the synthesis of a compound of the general type XII which can serve as metathesis catalyst according to the present invention.

It is not necessary to isolate and purify the catalyst precursor, but cationic complexes of the general type X–XII outlined above may be prepared in situ and directly used in metathesis reactions.

Examples of the reactons induced by the catalysts mentioned above include, but are not limited to, the ring closing metathesis (RCM) of acyclic dienes and polyenes, the metathesis of enynes and dienynes, the ring opening metathesis polymerization (ROMP) of cyclic olefins, the acyclic diene metathesis polymerization (ADMET) of acyclic dienes or polyenes, the depolymerization of olefinic polymers, and the cross metathesis of two or more olefins. The present invention also applies to combinations of these types of metathetic reactions, to domino processes thereof (Tietze, L. F. et al. Angew. Chem. Int. Ed. Engl. 1993, 32, 131), and to the dimerization or oligomerization of dienes followed by subsequent ring closure (cyclodi[oligo]merization).

The present invention applies to all types of olefins, independent of whether they are cyclic oracyclic, strained or unstrained, as well as to mixtures of olefins. The substrates can be used in polymer supported form or can be successively added to the reaction mixture.

The reactions are usually carried out by contacting the olefin substrate (neat or in solution) with the catalyst and optionally heating the mixture until the reaction is complete. The temperatures can range from –20° C. to about 150° C., preferably 10° C. to 90° C. The reaction time is not critical and can be from a few minutes to several days. The reactions are generally carried out under inert atmosphere, most preferably nitrogen, argon or $CO_2$, but the presence of oxygen may be tolerated under certain circumstances. The reaction can be carried out under irradiation of the reaction mixture e. g. by visible or UV-light, or by ultrasonic waves. The reaction can be performed in water or in the presence of water.

The ratio of catalyst to olefin substrate is not critical and can range from 1:5 to about 1:30000, preferably it is in the range of 1:20 to 1:2000.

Work-up of the reaction mixtures and purification is not critical and follows routine techniques depending on the specific properties of the products formed and/or the unreacted starting material. This may proceed either by distillation, filtration, chromatography, sublimation, crystallization, extraction as the preferred techniques.

Catalysts of the type described above are stable in the presence of a variety of functional groups, which include, but are not limited to, alcohol, acetal, ketal, keteneacetal, thiol, thioacetal, ketone, aldehyde, ester, ether, epoxide, gem-dialkyl group, amine, ammonium salt, amide, nitro, carboxylic acid, sulfide, disulfide, carbonate, carbamate, isocyanide, nitrile, urethane, urea, halogen, mine, sulfonate, sulfone, sulfoxide, silyl, stannyl, perfluoroalkyl, phosphonate, ferrocene, as well as oxygen-, nitrogen-, sulfur or phosphorous containing heterocycles.

In the case of ROMP, the present invention applies to the preparation of Vestenamer® (Dräxler, A. et al. Der Lichtbogen 1986, 35, 24) and Norsorex® (Ohm, R. F.; Chemtech 1980, 183).

In the case of oligomerization and polymerization reaction of appropriate monomers, the propagating carbene moiety was found to be stable and continues to polymerize additional aliquots of monomer for a period after the original amount of monomer has been consumed. The added monomer may be identical or not identical to the original one.

In case of RCM, the catalysts mentioned above apply to the formation of all ring sizes $x \geq 5$, including medium sized ($8 \leq x \leq 11$) and large ($x \geq 12$) rings, independent of whether the rings are carbocyclic or heterocyclic; the newly formed ring may be anellated to one or more pre-existing aromatic or non-aromatic carbo- or heterocyclic rings. The invention applies, but is not restricted, to the synthesis of products which may be used as pheromones, crown ethers, antibiotics, agro chemicals, pharmaceuticals for human and veterinary medicine, fragrances, flavors, perfume ingredients. Representative examples are compiled in Table 1.

In the case of the formation of macrocyclic rings which serve as perfume ingredients, the present invention applies to the synthesis of pentadecanolide or homologues, Arova 16 or homologues, civetone or homologues, muscenone or homologues, Exalton or homologues, muscenone or homologues, ethylenebrassylate (Musk 144) or homologues, and related macrocycles as described in Fürstner, A. et al., Synthesis 1997, 792 and U.S. application Ser. No. 08/767, 561 (16.12.1996).

In the case of the formation of medium or macrocyclic rings by RCM, the olefin substrates may be devoid of any conformational predisposition to ring closure as induced by various elements of structural preorganization.

Metathesis reactions catalyzed by the cationic vinylidene, allenylidene and higher cumulenylidene complexes of the general formula X–XII can be performed in any solvent or solvent mixture which does not inactivate the catalyst. This includes protic and aqueous solvents, compressed carbon dioxide (DE-A 19720798.7 (15.5.1997)), or perfluoroalkanes. However it is preferred to work under aprotic conditions in solvents with low coordination ability. Examples of preferred solvents include, but are not restricted to, dichloromethane, trichloromethane, 1,2-dichloroethane, trichloroethane, benzene, toluene, xylene, halobenzenes, cymene, tetrahydrofuran, diethylether, tert-butylmethylether, dimethoxyethane, petrol ether, hexane, cyclohexane, acetone. Depending on the specific physical properties of the substrates and products, the reactions can also be carried out with neat alkenes without any additional solvent added to the reaction mixture. Examples of cyclization reactions in preferred embodiments are given in Tables 1 and 2.

The concentration of the substrate (molarity, M) in a given solvent may be largely varied. Under certain circumstances the reaction can be carried out with neat substrates without any additional solvent. In the case of RCM leading to the formation of medium and macrocyclic rings it is preferred to work at molarities $M \leq 0.1$ in order to suppress the dimerization, cyclodimerization or polymerization of the diene substrates. In a preferred embodiment, solutions of the substrate and of the catalyst are combined at such a rate that the propensity of cyclization of the respective substrate is greater than that of a reactive encounter of two substrate molecules.

As a result of their stability in the presence of functional groups, the catalysts may be employed in the presence of one or more additives. Examples include, but are not limited to, metal salts, metal alkoxides, Lewis acids, perfluoroalkanes, phosphorous compounds, detergents, surfactants, silica, alumina, graphite, $CaCO_3$, or aluminum powder.

TABLE 1

RCM using catalyst (p-cymene)RuCl(PCy$_3$)(=C=C=CPh$_2$)$^+$PF$_6^-$ (2–5 mol %) in toluene at 80° C.

| Substrate | Product | Yield |
|---|---|---|
| | | 83% |
| | | 86% |
| | | 75% |
| | | 40% |

TABLE 1-continued

RCM using catalyst (p-cymene)RuCl(PCy$_3$)(=C=C=CPh$_2$)$^+$PF$_6^-$ (2–5 mol %) in toluene at 80° C.

| Substrate | Product | Yield |
|---|---|---|
| [macrocyclic diene ester] | [macrocyclic ester with internal alkene] | 90% |
| [diene amide] | [macrocyclic amide] | 55% |
| [sugar-containing diene] | [macrocyclic sugar product] | 85% |

TABLE 2

Cyclization reactions under various conditions using two different catalysts with most preferred embodiments:
A: (p-cymene)RuCl(PiPr$_3$)(=C=C=CPh$_2$)$^+$PF$_6^-$;
B: (p-cymene)RuCl(PCy$_3$)(=C=C=CPh$_2$)$^+$PF$_6^-$

[Ts-N(allyl)$_2$ → N-Ts-2,5-dihydropyrrole, catalyst (2.5 mol %)]

| Catalyst | Solvent | Additive | T (° C.) | t (h) | Yield (%)$^a$ |
|---|---|---|---|---|---|
| A | toluene | — | 80 | 3 | 66 |
| A | CH$_2$Cl$_2$ | — | 40 | 26 | 95 (76) |
| B | toluene | — | 80 | 3 | 79 |
| B | toluene | — | 80 | 4 | 100 (83) |
| B | toluene | cymene (50%) | 80 | 3 | 47 |
| B | toluene | PCy$_3$ (5%) | 80 | 3 | 31 |

$^a$GC-yield (isolated yield).

EXAMPLES

Abbreviations used: Cy=cyclohexyl; iPr=isopropyl; Ph=phenyl

The following prototype examples set forth the synthesis of catalysts and olefin metathesis reactions in preferred embodiments of the present invention. Further objectives and advantages of the present invention not mentioned above will become appearant from the examples which are not intended to limit its scope.

Example 1

(p-Cymene)RuCl(PCy$_3$)(=C=C=CPh$_2$)$^+$PF$_6^-$. In a Schlenk tube under argon are loaded NaPF$_6$ (0.099 g, 0.589 mmol, 1 eq.), the complex (p-cymene)RuCl$_2$(PCy$_3$) (0.344 g, 0.586 mmol) [prepared according to: Zelonka R. A. et al. *Can. J. Chem.* 1972, 50, 3063; Demonceau A. et al. *Macromolecules* 1997, 30, 3127], 1,1-diphenylprop-2-yn-1-ol (0.0243 g, 1.168 mmol, 2 eq.) and 30 ml of MeOH. The solution is stirred 3 h at room temperature, then the solvent is evaporated. The diphenylpropynol in excess is eliminated by washing the residue with 2×20 ml of Et$_2$O. The complex is then extracted with 2×10 ml of CH$_2$Cl$_2$ (separation from NaCl formed during the reaction), and the solution is evaporated. The violet powder obtained is washed again with 20 ml of Et$_2$O, filtered and dried under vacuum. Violet powder (97%). $^{31}$P NMR (CDCl$_3$, 81.015 MHz) d (ppm): 58.81 (PCy$_3$); −140.80 (sp, J$_{PF}$=710 Hz, PF$_6^-$); $^1$H NMR (CDCl$_3$, 200.132 MHz) d (ppm): 7.87 (md, 4H, J=7.2, Ph); 7.75 (m, 2H, Ph); 7.48 (m, 4H, Ph); 6.63 (md, 1H, J=6.6, H arom p-cym.); 6.47 (md, 1H, J=6.5, H arom p-cym.); 6.11 (md, 1H, J=6.7, H arom p-cym.); 6.02 (md, 1H, J=5.9, H arom p-cym.); 2.72 (hept, 1H, CH iPr p-cym.); 2.20 (m broad, 3H, cyclohexyl H-1); 2.20 (s, 3H, Me); 1.29 (m, 6H, CH$_3$ iPr p-cym.); 2.1–0.9 (m, 30H, cyclohexyl); IR (KBr, ν cm$^{-1}$): 3057, 3026 (=CH); 2932, 2854 (C—H). 1959 (Ru=C=C=C); 1594, 1490, 1448 (Ph); 840, 557 (PF$_6^-$); Calcd. for C$_{34}$H$_{45}$ClF$_6$P$_2$Ru: C, 53.30; H, 5.92; P, 8.09. Found: C, 52.19; H, 5.73; P, 8.05%.

Example 2

(p-Cymene)RuCl(PiPr$_3$)(=C=C=CPh$_2$)$^+$PF$_6^-$. Following the procedure described in example 1 with 0.043 g of NaPF$_6$ (0.256 mmol, 1 eq.), 0.117 g of the complex (p-cymene)RuCl$_2$(PiPr$_3$) (0.251 mmol, 1 eq.), 0.063 g of 1,1-diphenylprop-2-yn-1-ol (0.302 mmol, 1.2 eq.) and 15 ml of MeOH in 4 h at room temperature. The diphenylpropynol in excess is eliminated by washing the residue with 10 ml of Et$_2$O. The complex is then washed with 3×20 ml of toluene and extracted with 20 ml of CH$_2$Cl$_2$. Violet powder, 95%. $^{31}$P NMR (CDCl$_3$, 81.015 MHz) d (ppm): 68.14 (PiPr$_3$); −143.69 (sp, $^1$J$_{PF}$=712 Hz, PF$_6^-$); $^1$H NMR (CDCl$_3$, 200.132 MHz) d (ppm): 7.86 (md, 4H, J=7.1, Ph); 7.75 (m, 2H, Ph); 7.48 (m, 4H, Ph); 6.62 (md, 1H, J=6.9, H arom p-cym.); 6.54 (md, 1H, J=6.9, H arom p-cym.); 6.09 (m, 2H, H arom p-cym.); 3.05–2.50 (m, 4H, CH iPr.); 2.33 (s, 3H, CH$_3$ p-cym.); 1.51 (d, 3H, J=7.2 CH$_3$ iPr p-cym.); 1.42 (d, 3H, J=7.2 CH$_3$ iPr p-cym.); 1.35–1.10 (m, 18H, CH$_3$ P(iPr)$_3$); IR (KBr, ν cm$^{-1}$): 3058 (=CH); 2967, 2932, 2876 (C—H); 1945 (Ru=C=C=C); 1587, 1487 (Ph); 839, 557 (PF$_6^-$); MS: 621.2 (M+−PF$_6$).

Example 3

N-Tosyl-2,5-dihydropyrrole. A solution of N,N-diallyltosylamide (259 mg, 1.03 mmol) and the allenylidene complex (p-cymene)RuCl(PCy$_3$)(=C=C=CPh$_2$)$^+$PF$_6^-$ (22 mg, 0.0248 mmol, 2.4 mol %) in toluene (5 mL) is stirred for 4 h at 80 °C. The solvent is evaporated and the crude product purified by flash chromatography using ether:pentane (1:4) as the eluent. This affords the title compound as a colorless solid (191 mg, 83%). $^1$H NMR (200 MHz, CDCl$_3$): δ=2.40 (s, 3H), 4.10 (s, 4H), 5.63 (s, 2H), 7.30 (dm, 1H, J=8.6, 0.7), 7.70 (dm, 1H, J=8.3, 1.9). $^{13}$C NMR (50 MHz, CDCl$_3$): δ=21.1, 54.5, 125.1, 129.3, 129.4, 139.2, 143.1. IR (KBr): 3093, 3047, 2951, 2909, 2854, 1928, 1817, 1595, 1540. MS (rel. Intensity): 223 (28, [M$^+$]), 155 (28), 91 (72), 68 (100), 41 (19). C$_{11}$H$_{13}$NO$_2$S (223.3): calcd. C, 59.17, H, 5.83, N, 6.27, S 14.36; found: C, 59.26, H, 5.91, N, 6.22, S, 14;36.

Example 4

N-Tosyl-2,5-dihydropyrrole. A solution of N,N-diailyltosylamide (259 mg, 1.03 mmol) and the allenylidene complex (p-cymene)RuCl(PiPr$_3$)(=C=C=CPh$_2$)$^+$PF$_6^-$ (22 mg, 0.0248 mmol, 2.4 mol %) in CH$_2$Cl$_2$ (5 mL) is refluxed for 26 h under argon. The solvent is evaporated and the crude product purified by flash chromatography using ether:pentane (1:4) as the eluent. This affords the title compound as a colorless solid (76%), the spectral data of which are identical to those reported above.

Example 5

Pentadec-10-enolide. Solutions of 5-hexen-1-yl 10-undecenoate (134 mg, 0.503 mmol) and complex (p-cymene)RuCl(PCy$_3$)(=C=C=CPh$_2$)$^+$PF$_6^-$ (22 mg, 0.0248 mmol, 4.9 mol %) in toluene (50 mL each) are added over a period of 24 h via two dropping funnels to toluene (25 mL) at 80° C. Stirring is continued for another 16 h at that temperature prior to evaporation of the solvent and purification of the residue by flash chromatography using ether:pentane (1:20) as the eluent. This affords the macrocycle as a colorless syrup (108 mg, 90%). $^1$H NMR (200 MHz, CDCl$_3$): δ=5.45–5.28 (m, 2H), 4.18–4.07 (m, 2H), 2.37–229 (m, 2H), 2.10–2.00 (m, 4H), 1.72–1.54 (m, 4H), 1.49–1.30 (m, 10H). 13C NMR (50 MHz, CDCl$_3$): δ=173.9, 131.7, 130.4, 130.1, 129.6, 64.1, 64.0, 34.7, 33.9, 32.0, 29.1, 28.4, 28.4, 28.3, 28.2, 28.1, 28.0, 27.9, 27.6, 27.2, 27.1, 26.6, 26.5, 25.4, 25.2. IR (KBr): 3000, 2928, 2856, 1736, 1461, 1385, 1346, 1252, 1234, 1168, 1152, 1113, 1085, 1024, 969, 719. MS (rel. Intensity): 238 ([M$^+$], 20), 210 (18), 109 (17), 96 (49), 82 (100), 67 (64),55 (64). C$_{15}$H$_{26}$O$_2$ (228.37): calcd. C, 75.58, H, 10.99; found: C, 75.65, H, 11.08.

Example 6

3-(2,5-Dihydrofuran-3-yl)-2,5-dihydrofuran. A mixture of 1,4-bis(allyloxy)-2-butyne (157 mg, 1.02 mmol) and (p-cymene)RuCl(PCy$_3$)(=C=C=CPh$_2$)$^+$PF$_6^-$ (22 mg) in toluene (5 mL) is stirred for 3 h under argon at 80° C. The solvent is evaporated and the residue purified by flash chromatography using diethylether/pentane (1/4) as eluent. This affords the title compound as white solid (110 mg, 86%). $^1$H NMR (200 MHz, CDCl$_3$): δ=4.70 (br. S, 8H), 5.59 (s, 2H). $^{13}$C NMR (50 MHz, CDCl$_3$): δ=74.7, 76.0, 122.5, 131.4.

Example 7

N-Tosyl-2,5-dihydropyrrole: Metathesis under Photochemical Irradiation. A solution of N,N-diallyltosylamide (251 mg, 1 mmol) and the allenylidene complex (p-cymene) RuCl(PCy$_3$)(=C=C=CPh$_2$)$^{30}$ PF$_6^-$ (23 mg, 0.0259 mmol, 2.6 mol %) in toluene (5 ml) is stirred at room temperature under ultraviolet (UV) irradiation (Hg lamp, 300 nm) for 5 hours under argon. The solvent is evaporated and the crude product is purified by flash chromatography using ether:pentane (1:4) as the eluent. The title compound was obtained as a colorless solid (180 mg, 81%), the spectral data of which are identical to those reported above.

Example 8

N-Tosyl-2,5-dihydropyrrole: Metathesis with a Catalyst Pre-Activated by Photochemical Irradiation. A solution of N,N-diallyltosylamide (248 mg, 0.987 mmol) and the allenylidene complex (p-cymene)RuCl(PCy$_3$) (=C=C=CPh$_2$)$^+$PF$_6^-$ (23 mg, 0.0259 mmol, 2.63 mol %) in toluene (5 ml) is stirred at room temperature under UV irradiation (Hg lamp, 300 nm) for 30 minutes under nitrogen, then stirred for 3 hours at 50° C. without UV irradiation. The solvent is evaporated and the crude product is purified by flash chromatography using ether:pentane (1:4) as the eluent. The title compound was obtained as a colorless solid (156 mg, 71%), the spectral data of which are identical to those reported above.

Example 9

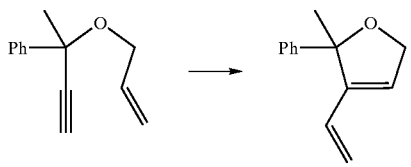

2-Methyl-2-phenyl-3-vinyl-2,5-dihydrofuran. A solution of 2-allyloxy-2-phenylbut-3-yne (368 mg, 1.97 mmol) and the allenylidene complex (p-cymene)RuCl(PCy$_3$)(=C=C=CPh$_2$)$^+$PF$_6^-$ (43 mg, 0.0485 mmol, 2.5 mol %) in toluene (10 ml) is stirred for 24 hours at 80° C. under nitrogen. The solvent is evaporated and the crude product is purified by flash chromatography using ether:pentane (1:10) as the eluent. The title compound was obtained as a yellowish liquid (283 mg, 77%). $^1$H NMR (200 MHz, CDCl$_3$): d=1.79 (s, 3H, CH$_3$); 4.76 (m, 2H, J=0.8, OCH$_2$); 5.02 (d, 1H, J=11.2, =CH$_2$); 5.06 (d, 1H, J=17.8, =CH$_2$); 5.98 (m, 1H, C=CH); 6.21 (ddd, 1H, J=17.8, 11.2 and 0.8, =CH); 7.20–7.47 (m, 5H, Ph). $^{13}$C NMR (50 MHz, CDCl$_3$): d=24.4 (CH$_3$); 73.1 (OCH$_2$); 89.8 (C); 117.1 (=CH$_2$); 124.3 (=CH); 126.1 (Ph); 128.3. (=CH); 128.6, 128.9 (Ph); 144.5 (C); 144.7 (C Ph). IR (NaCl windows): 3088, 3060, 3029, 2979, 2832, 2837, 1821, 1644, 1620, 1596, 1492, 1448,1370, 1344, 1239, 1201, 1139, 1068, 1021, 991, 913, 865, 807, 763, 701. MS (rel. Intensity): 186 ([M$^+$], 8); 172 (19); 171 (100); 153 (15); 144 (7); 143 (43); 142 (19); 128 (50); 127 (11); 115 (27); 109 (19); 105 (23); 91 (20); 81 (12); 79 (14); 78 (11); 77 (54); 76 (7); 66 (15); 65 (26); 63 (13); 55 (13); 53 (10); 52 (7); 51 (33); 50 (9); 43 (49); 40 (12); 39 (30); 27 (11). C$_{13}$H$_{14}$O (186.27): calcd. C, 83.83, H, 7.66; found: C, 83.54, H, 7.58.

Example 10

2-Methyl-2-phenyl-3-vinyl-2,5-dihydrofuran: Metathesis under Photo-chemical Irradiation. A solution of 2-allyloxy-2-phenylbut-3-yne (371 mg, 1.99 mmol) and the allenylidene complex (p-cymene)RuCl(PCy$_3$)(=C=C=CPh$_2$)$^+$PF$_6^-$ (44 mg, 0.0496 mmol, 2.5 mol %) in toluene (10 ml) is irradiated with UV light (Hg lamp, 300 nm) for 30 minutes at room temperature under nitrogen, then stirred for 4 hours at 80° C. without UV irradiation. The solvent is evaporated and the crude product is purified by flash chromatography using ether:pentane (1:10) as the eluent. This affords the title compound as a yellowish liquid (313 mg, 84%), the spectral data of which are identical to those reported above.

Example 11

N-Tosyl-2,5-dihydropyrrole: Effect of Counter Anion. A solution of N,N-diallyltosylamide (253 mg, 1.01 mmol) and the allenylidene complex (p-cymene)RuCl(PCy$_3$)(=C=C=CPh$_2$)$^+$B(C$_6$H)$_4$ (26 mg, 0.0246 mmol, 2.44 mol %) in toluene (5 ml) is stirred for 5 hours at 80° C. under nitrogen. The solvent is evaporated and the crude product is purified by flash chromatography using ether:pentane (1:4) as the eluent. This affords the title compound as a colorless solid (186 mg, 83%), the spectral data of which are identical to those reported above.

Example 12

N-Tosyl-2,5-dihydropyrrole: Effect of Counter Anion. A solution of N,N-diallyltosylamide (127 mg, 0.505 mmol) and the allenylidene complex (p-cymene)RuCl(PCy$_3$)(=C=C=CPh$_2$)$^+$CF$_3$SO$_3^-$ (11 mg, 0.0124 mmol, 2.45 mol %) in toluene (2.5 ml) is stirred for 1 hour at 80° C. under nitrogen. The solvent is evaporated and the crude product is purified by flash chromatography using ether:pentane (1:4) as the eluent. This affords the title compound as a colorless solid (103 mg, 91%), the spectral data of which are identical to those reported above.

Using the same conditions, stirring the solution for 19 hours at room temperature affords 94% conversion, from which 90% of the title compound can be isolated.

Example 13

N-Tosyl-2,5-dihydropyrrole: Influence of the Allenylidene Moiety and of the Counter Anion. A solution of N,N-diallyltosylamide (127 mg, 0.505 mmol) and the allenylidene complex (p-cymene)RuCl(PCy$_3$)(=C=C=C(p-Cl—C$_6$H$_4$)$_2$)$^+$BF$_4^-$ (12 mg, 0.0134 mmol, 2.65 mol %) in toluene (2.5 ml) is stirred for 5 hours at 80° C. under nitrogen. The solvent is evaporated. GC-MS and $^1$H NMR measurement on the crude show a conversion of 90% in the title compound.

Example 14

Polynorbornene. A solution of norbornene (500 mg, 5.31 mmol) and the allenylidene complex (p-cymene)RuCl(PCy$_3$)(=C=C=CPh$_2$)$^+$PF$_6^-$ (7 mg, 0.0079 mmol, 0.15 mol %) in toluene (3 ml) is stirred at room temperature under nitrogen until the solution becomes a jelly (c.a. 5 minutes). The crude mixture is then extracted with toluene and a slightly yellow solid is obtained by precipitation in methanol (500ml) (368. mg, 74%). $^1$H NMR (200 MHz, CDCl$_3$): d=1.10–1.50 (m, 2H); 1.5–2.2 (m, 4H); 2.2–2.8 (m, 2H); 5.1–5.4 (m, 2H). $^{13}$C NMR (50 MHz, CDCl$_3$): d=32.24 (CH$_2$); 41.41 (CH$_2$); 43.17 (CH); 133.07 (=CH).

Example 15

Polydicyclopentadiene. A mixture of dicyclopentadiene (996 mg, 7.53 mmol) and the allenylidene complex (p-cymene)RuCl(PCy$_3$)(=C=C=CPh$_2$)$^+$PF$_6^-$ (10 mg, 0.0113 mmol, 0.15 mol %) is heated without solvent for 90 minutes at 80° C. under nitrogen. This affords the polymer as an insoluble brown solid (440 mg, 44%).

Example 16

N-Tosyl-2,5-dihydropyrrole: Metathesis under Sonochemical Irradiation. A solution of N,N-diallyltosylamide (179 mg) and the allenylidene complex (p-cymene)RuCl(PCy$_3$)(=C=C=CPh$_2$)$^+$PF$^-$ (6 mg) in CH$_2$Cl$_2$ (20 ml) is sonicated at room temperature with an ultrasound cleaning bath (Brandelin Sonorex RK 514) under argon for 4 h. The solvent is evaporated and the crude product is purified by flash chromatography using hexane-:ethyl acetate (1:10) as the eluent. The title compound was obtained as a colorless solid (139 mg, 87%), the spectral data of which are identical to those reported above.

Example 17

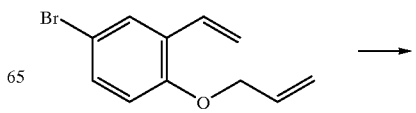

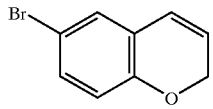

6-Bromo-2H-1-benzopyran. A solution of 2-allyloxy-5-bromostyrene (416 mg) in toluene (20 ml) is added dropwise to a solution of the allenylidene complex (p-cymene)RuCl (PCy$_3$)(=C=C=CPh$_2$)$^+$PF$_6^-$ (54 mg) in toluene (5 ml) over a period of 1.5 h at 80° C. After stirring at that temperature for another 16 h, the solvent is evaporated and the crude product purified by flash chromatography affording the title compound (341 mg, 93%). $^1$H NMR (200 MHz, CDCl$_3$): d=7.15 (dd, 1H), 7.04 (d, 1H), 6.62 (d, 1H), 6.31 (dt, 1H), 5.77 (dt, 1H), 4.86 (dd, 2H).

Example 18

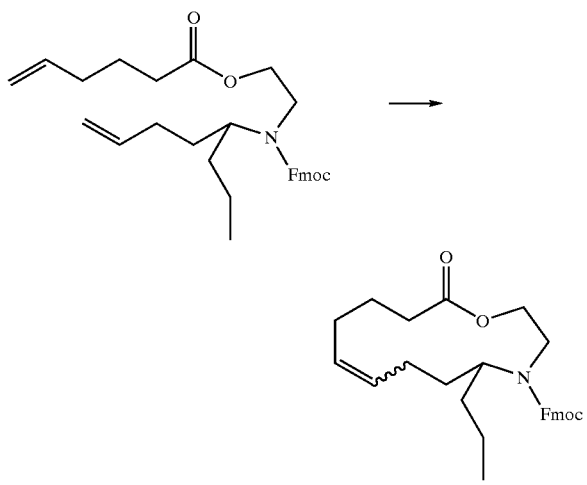

N-(9-Fluorenylmethoxycarbonyl)-5-propyl-1-oxa-4-azacyclotridec-8-en-13-one. (Fmoc=9-Fluorenylmethoxycarbonyl) Solutions of 5-hexenoic acid [N-(Fmoc)-2-(1-propyl-pent-4-enylamino)]-ethyl ester (140 mg; prepared as described in Fürstner, A. et al. *Synthesis* 1997, 792) and of the allenylidene complex (p-cymene)RuCl(PCy$_3$)(=C=C=CPh$_2$)$^+$PF$_6^-$ (12 mg) in toluene (50 ml each) are combined over a period of 8 h. The mixture is warmed to 80° C. for 18 h. After that time, the catalyst is re-plenished (7 mg) and stirring is continued for another 18 h at that temperature. Evaporation of the solvent and flash chromatography of the crude product with hexane:ethyl acetate (10:1→8:1) affords the title compound (103 mg, 78%), the data of which are in accordance with those reported in the literature cited above. mp 148.5–149.5° C. $^1$H NMR (200 MHz, CDCl$_3$, rotamers) δ=7.77–7.70 (m, 2H), 7.59–7.56 (m, 2H), 7.4–7.23 (m, 4H), 5.49–5.32 (m, 1H), 5.19–5.07 (m, 1H), 4.78–4.47 (m, 2H), 3.47 (m, 4H), 3.09–2.74 (m, 2H), 2.35–1.89 (m, 6H), 1.65 (m, 1H), 1.46–0.69 (m, 10H). $^{13}$C NMR (50 MHz, CDCl$_3$, rotamers) δ=174.0, 157.1, 156.9, 144.9, 144.0, 143.9, 141.5, 141.4, 141.3, 131.5, 131.3, 127.6, 127.5, 127.2, 127.1, 127.0, 126.9, 124.7, 124.6, 124.5, 119.9, 119.9, 119.8, 66.4, 63.3, 62.8, 56.3, 47.6, 47.4, 41.2, 40.7, 35.8, 34.0, 32.9, 32.5, 31.5, 31.4, 25.3, 25.1, 25.0, 24.4, 24.3, 22.6, 19.3, 14.0, 13.8, 13.7.

Example 19

N-Tosyl-2,5-dihydropyrrole: Increase of the catalytic activity of the allenylidene complexes by addition of an acid. A solution of N,N-diallyltosylamide (125 mg, 0.497 mmol), the allenylidene complex (p-cymene)RuCl(PCy$_3$)(=C=C=CPh$_2$)$^+$PF$_6^-$ (11 mg, 0.0124 mmol, 2.5 mol %) and tetrafluoroboric acid diethylether complex (54% wt., 0.034 ml, 0.247 mmol, 49.7 mol %) in toluene (2.5 ml) is stirred for 1 hour at room temperature under nitrogen. The solvent is evaporated. GC-MS and $^1$H NMR measurement on the crude mixture show a conversion of 80% in the title compound.

This example should be compared with RCM of the same substrate in the absence of additives (EXAMPLE 3) which requires heating at 80° C. for 4 hours to yield 83% of the title compound.

Example 20

N-Tosyl-2,5-dihydropyrrole: Increase of the catalytic activity of the allenylidene complexes by addition of an acid. A solution of N,N-diallyltosylamide (125 mg, 0.497 mmol), the allenylidene complex (p-cymene)RuCl(PCy$_3$)(=C=C=CPh$_2$)$^+$PF$_6^-$ (11 mg, 0.0124 mmol, 2.5 mol %) and chlorohydric acid (1 M solution in diethylether, 0.250 ml, 0.25 mmol, 50 mol %) in toluene (2.5 ml) is stirred for 22 hours at room temperature under nitrogen. The solvent is evaporated. GC-MS and $^1$H NMR measurement on the crude mixture show a conversion of 69% in the title compound.

This example should be compared with RCM of the same substrate in the absence of additives (EXAMPLE 3) which requires heating at 80° C. for 4 hours to yield 83% of the title compound.

Example 21

(p-Cymene)RuCl(PCy$_3$)(=C=C=CPh$_2$)$^+$CF$_3$SO$_3^-$. A Schlenk tube is charged with CF$_3$SO$_3$Ag (0.173 g, 0.673 mmol, 1.04 eq.), the complex (p-cymene)RuCl$_2$(PCy$_3$) (0.379 g, 0.65 mmol) [prepared according to: Zelonka R. A. et al., *Can. J. Chem.* 1972, 50, 3063; Demonceau A. et al. *Macromolecules* 1997, 30, 3127] and 30 ml of CH$_2$Cl$_2$ under a nitrogen atmosphere. The solution is stirred 1.5 hours at room temperature, then the solvent is evaporated. The complex of formula [(p-cymene)RuCl(PCy$_3$]$^+$CF$_3$SO$_3^-$ is obtained as a brown powder after washing the crude residue with a 1:1 mixture of ether:pentane (20 ml) (0.431 g, 95%). Part of this compound (0.128 g, 0.183 mmol) is dissolved in 15 ml of CH$_2$Cl$_2$ under nitrogen and 1,1-diphenylpropynol (0.06 g, 0.288 mmol, 1.6 eq.) is added in one portion. The mixture is stirred at room temperature for 1 hour, then the solvent is evaporated. The powder thus obtained is washed twice with 20 ml of diethylether and dried under reduce pressure. The title complex is obtained as a violet powder (0.155 g, 95%). $^{13}$P NMR (CDCl$_3$, 91.01 MHz) δ (ppm): 59.21 (PCy$_3$); $^1$H NMR (200.132 MHz, CDCl$_3$) δ (ppm): 7.86 (d, 4H, J=7.4, Ph); 7.74 (t, 2H, J=7.4, Ph); 7.47 (t, 4H, J=7.4, Ph); 6.69 (d, 1H, J=5.8, H arom. p-cym.); 6.52 (d, 1H, J=5.7, H arom. p-cym.); 6.29 (d, 1H, J=6.4, H arom. p-cym.); 6.1 (d, 1H, J=6.4, H arom. p-cym.); 2.71 (hept, 1H, CH iPr p-cym.); 2.28 (m broad, 3H, cyclohexyl H-1); 2.21 (s, 3H, Me); 1.30 (d, 6H, J=6.9, CH$_3$ p-cym.); 2.1–1.0 (m, 30H, cyclohexyl).

Example 22

(p-Cymene)RuCl(PCy$_3$)(=C=C=CPh$_2$)$^+$BF$_4^-$. A Schlenk tube is charged with AgBF$_4$ (0.07 g, 0.359 mmol, 1 eq.), the complex (p-cymene)RuCl$_2$(PCy$_3$) (0.21 g, 0.359 mmol) [prepared according to: Zelonka R. A. et al., *Can. J. Chem.* 1972, 50, 3063; Demonceau A. et al. *Macromolecules*

1997, 30, 3127], the 1,1-diphenylpropynol (0.077 g, 0.37 mmol, 1.03 eq.) and 20 ml of $CH_2Cl_2$ under a nitrogen atmosphere. The solution is stirred 1 hour at room temperature, then the solvent is evaporated. The powder thus obtained is washed twice with 20 ml of diethylether and dried under reduce pressure. The title complex is obtained as a violet powder (0.265 g, 89%). $^{31}P$ NMR ($CDCl_3$, 91.01 MHz) δ (ppm): 59.08 ($PCy_3$); $^1H$ NMR (200.132 MHz, $CDCl_3$) δ (ppm): 7.87 (d, 4H, J=7.4, Ph); 7.74 (t, 2H, J=7.4, Ph); 7.47 (t, 4H, J=7.4, Ph); 6.69 (d broad, 1H, J=6.5, H arom. p-cym.); 6.51 (d broad, 1H. J=6.5, H arom. p-cym.); 6.24 (d, 1H, J=6.5, H arom. p-cym.); 6.06 (d, 1H, J=6.5, H arom. p-cym.); 2.71 (hept, 1H, CH iPr p-cym.); 2.25 (m broad, 3H, cyclohexyl H-1); 2.20 (s, 3H, Me); 1.30 (d, 6H, J=6.9, $CH_3$ p-cym.); 2.1–1.0 (m, 30H, cyclohexyl); IR (KBr, ν $cm^{-1}$): 3060 (=CH); 2960, 2850 (C—H); 1958 (Ru=C=C=C); 1590,1490 (Ph); 1060 ($BF_4^-$).

What is claimed is:

1. A process for a metathesis reaction, comprising contacting an olefin with a catalyst, wherein the catalyst comprises vinylidene, allenylidene and higher cumulenylidene complexes of the general formula:

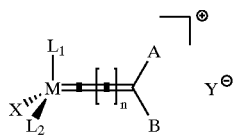

wherein

M is Ru or Os;

X is an anionic ligand;

$L_2$ is selected from the group consisting of phosphine, sulfonated phosphine, fluorinated phosphine, functionalized phosphine bearing up to three aminoalkyl-, ammoniumalkyl-, alkoxyalkyl-, alkoxycarbonylalkyl-, hydroxycarbonylalkyl-, hydroxyalkyl-, ketoalkyl-groups, phosphite, phosphinite, phosphonite, arsine, and stibene;

$L_1$ is a neutral π-bond ligand;

A and B are independently selected from hydrogen or from the group consisting of C1–C20 alkyl, aryl, C2–C20 alkenyl, alkynyl, C1–C20 alkoxy, carboxylate, carbamate, C2–C20 alkenyloxy, alkynyloxy, aryloxy, alkoxycarbonyl, C1–C20 alkylthio, alkylsulfonyl, alkylsulfinyl, arylthio, arylsulfonyl, arylsulfinyl, alkylamido, alkylamino, each of which is optionally substituted with C1–C10 alkyl, perfluoroalkyl, aryl, alkoxy or with halogen;

$Y^-$ is a non-coordinating anion; and n is 0–5.

2. The process according to claim 1, in which the catalyst is prepared in situ and used in the metathesis reaction without prior isolation.

3. The process according to claim 1, in which the olefin is cyclic or acyclic with or without one or more functional groups.

4. The process according to claim 1, in which the olefin is bound to a polymer.

5. The process according to claim 1, in which the reaction is carried out in the absence of solvents with neat alkenes.

6. The process according to claim 1, in which the reaction is carried out in a solvent or solvent mixture which does not inactivate the catalyst.

7. The process according to claim 1, which is carried out in the presence of one or more additives.

8. The process according to claim 1, which is carried out in the presence of a BrØnsted acid.

9. The process according to claim 1, in which the reaction is carried out under irradiation.

10. The process according to claim 9, where the reaction is irradiated by visible or UV-light.

11. The process according to claim 9, where the reaction is irradiated by ultrasonic waves.

12. The process according to claim 1, in which the metathesis reaction leads to a cyclic product of any ring size x ≧5 by ring closing olefin metathesis (RCM), enyne metathesis, metathesis depolymerization reactions, or combinations or domino processes thereof, independent of whether the product is carbocyclic or heterocyclic.

13. The process according to claim 12, in which the product is anellated to one or more pre-existing aromatic or non-aromatic carbo- or heterocyclic rings.

14. The process according to claim 12, in which the cyclic product comprises one or more medium sized (8≦x≦11) or macrocyclic (x≧12) rings.

15. The process according to claim 12, wherein the cyclic product is used as a pheromone, crown ether, antibiotic, agro chemical, pharmaceutical for human or veterinary medicine, fragrance, flavor, or perfume ingredient.

16. The process according to claim 1, in which the metathesis reaction affords a polymeric product by ring opening metathesis polymerization (ROMP) of strained or unstrained cyclic olefin monomers or by acyclic diene metathesis polymerization (ADMET).

17. The process according to claim 16, in which the polymeric product is produced by addition of at least one added monomer to the reaction after an amount of starting monomer has been consumed; said added monomer can be identical or not identical to the starting monomer.

18. The process according to claim 16, in which the polymeric product is a polycyclooctene or a polynorbornene.

19. The process according to claim 1, wherein the metathesis reaction is a cross metathesis of two or more olefins.

20. A compound of the general formula XII:

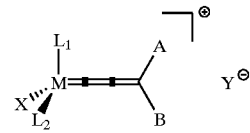

XII wherein

M is Ru or Os;

X is an anionic ligand;

$L_1$ is a neutral π-bond ligand;

$L_2$ is selected from the group consisting of phosphines, arsine and stibenes bearing one or more secondary alkyl, tertiary alkyl, or cycloalkyl groups;

A, B are independently selected from hydrogen or from the group consisting of C1–C20 alkyl, aryl, C2–C20 alkenyl, alkynyl, C1–C20 alkoxy, carboxylate, carbamate, C2–C20 alkenyloxy, alkynyloxy, aryloxy, alkoxycarbonyl, C1–C20 alkylthio, alkylsulfonyl, alkylsulfinyl, arylthio, arylsulfonyl, arylsulfinyl, alkylamido, alkylamino, each of which is optionally substituted with C1–C10 alkyl, perfluoroalkyl, aryl, alkoxy or with halogen; and $Y^-$ is a non-coordinating anion.

21. A compound according to claim 20, wherein

M is Ru;

X is halogen;

$L_1$ is benzene or substituted benzene;

L₂ is selected from the group consisting of phosphines, arsine and stibenes bearing one or more secondary alkyl, tertiary alkyl, or cycloalkyl groups;

A, B are independently selected from the group consisting of C1–C20 alkyl and aryl and $Y^-$ is a non-coordinating anion.

22. A compound according to claim 20, wherein

M is Ru;

X is chloride;

$L_1$ is p-cymene;

$L_2$ is selected from the group consisting of P(isopropyl)₃, P(cyclohexyl)₃, P(cyclopentyl)₃, P(neopentyl)₃, and P(tertiobutyl)₃;

A, B are aryl or substituted aryl; and $Y^-$ is selected from the group consisting of $PF_6^-$, $BF_4^-$, $BPh_4^-$, $F_3CSO_3^-$, $H_3CSO_3^-$, $ClO_4^-$, $SO_4^-$, $NO_3^-$, $PO_4^-$, $CF_3COO^-$, $B(C_6F_5)_4^-$, $RSO_3^-$, and $RCOO^-$ with R being selected from the group consisting of C1–C20 alkyl and aryl.

23. A process for methathesis reaction, comprising contacting an olefin with a catalyst, wherein the catalyst comprises a compound of the formula XII according to claim 20.

24. The process according to claim 15, wherein the cyclic product is used as a perfume ingredient, and the cyclic product is selected from the group consisting of pentadecanolide or homologs thereof, dodecanedioc acid ethylene ester or homologs thereof, civetone or homologs thereof, muscone or homologs thereof, cyclopentadecanone or homologs thereof, muscenone or homologs thereof, and ethylenebrassylate or homologs thereof.

25. A process for preparing a compound of the formula XII:

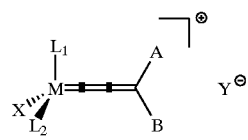

XII wherein

M is Ru;

X is halogen;

$L_1$ is benzene or substituted benzene;

$L_2$ is selected from the group consisting of phosphines, arsine and stibenes bearing one or more secondary alkyl, tertiary alkyl, or cycloalkyl groups;

A, B are independently selected from the group consisting of $C_1$–C20 alkyl and aryl; and $Y^-$ is a non-coordinating anion;

said process comprising condensing a compound of the formula $L_1RuX_2L_2$ and an alkynol of the formula $HC{\equiv}C{-}C(OH)AB$ or a derivative thereof.

26. The process according to claim 1, wherein $L_1$ is a neutral π-bond ligand selected from the group consisting of monocyclic or polycyic arenes, substituted arenes and heteroarenes.

27. The process according to claim 3, wherein the functional group is selected from the group consisting of alcohol, acetal, ketal, ketenacetal, thiol, thioacetal, ketone, aldehyde, ester, ether, epoxide, gem-dialkyl group, amine, ammonium salt, amide, nitro, carboxylic acid, sulfide, disulfide, carbonate, carbamate, isocyanide, nitrile, urethane, urea, halogen, imine, sulfonate, sulfone, sulfoxide, silyl, stannyl, perfluoroalkyl, phosphonate, ferrocene, and oxygen-, nitrogen-, sulfur or phosphorous containing heterocycles.

28. The process according to claim 7, wherein the one or more additives are selected from the group consisting of metal salts, metal alkoxides, Lewis acids, perfluoroalkanes, phosphorus compounds, detergents, surfactants, silica, alumina, graphite, $CaCO_3$ and aluminum powder.

29. The process according to claim 20, wherein $L_1$ is a neutral π-bond ligand selected from the group consisting of monocyclic or polycyclic arenes, substituted arenes and heteroarenes.

* * * * *